United States Patent
Hines et al.

(10) Patent No.: US 7,618,662 B2
(45) Date of Patent: Nov. 17, 2009

(54) USE OF NATURAL PLANT EXTRACTS IN COSMETIC COMPOSITIONS

(75) Inventors: Michelle D. Hines, Lawnside, NJ (US); Michele C. Duggan, Middletown, NY (US); Ralph R. Binetti, Danbury, CT (US)

(73) Assignee: Avon Products, Inc, New York, NY (US)

( * ) Notice: Subject to any disclaimer, the term of this patent is extended or adjusted under 35 U.S.C. 154(b) by 0 days.

(21) Appl. No.: 11/021,047

(22) Filed: Dec. 22, 2004

(65) Prior Publication Data

US 2006/0134231 A1 Jun. 22, 2006

(51) Int. Cl.
*A61K 36/67* (2006.01)
*A61K 36/00* (2006.01)

(52) U.S. Cl. ...................................... 424/734; 424/725
(58) Field of Classification Search ........................ None
See application file for complete search history.

(56) References Cited

U.S. PATENT DOCUMENTS

| | | | |
|---|---|---|---|
| 4,379,454 A | 4/1983 | Campbell et al. |
| 4,820,724 A | 4/1989 | Nimni |
| 4,956,171 A | 9/1990 | Chang |
| 5,146,846 A | 9/1992 | Lee et al. |
| 5,223,262 A | 6/1993 | Kim et al. |
| 5,770,222 A | 6/1998 | Unger et al. |
| 5,834,513 A | 11/1998 | Ptchelintsev et al. |
| 5,847,003 A | 12/1998 | Ptchelintsev et al. |
| 6,573,299 B1 * | 6/2003 | Petrus ........................ 514/558 |

FOREIGN PATENT DOCUMENTS

| | | | |
|---|---|---|---|
| JP | 1036217 A | * | 2/1998 |
| JP | 10036217 A | * | 2/1998 |
| JP | 410036217 | | 2/1998 |
| JP | 2000290165 A | * | 10/2000 |
| JP | 2003089630 | * | 3/2003 |

OTHER PUBLICATIONS 2002. environmentalnepal.com.np/news.*
environmentnepal.com.*

* cited by examiner

*Primary Examiner*—Christopher R Tate
*Assistant Examiner*—Melenie McCormick
(74) *Attorney, Agent, or Firm*—Joan M. McGillycuddy; Charles J. Zeller; Anthony M. Santini

(57) ABSTRACT

The present invention describes compositions and methods for treating, preventing and improving the appearance of skin, particularly, treating, preventing, ameliorating, reducing and/or eliminating loss of subcutaneous fat in the skin, wherein the compositions include natural plant constituents that stimulate lipid synthesis. The plant extracts are preferably derived from *Rhinacanthus nasutus, Humulus scandens, Sesbania grandiflora, Amorphophallus campanulatu, Pouzolzia pentandra*, and *Piper betel*, and any combinations thereof. The compositions are preferably applied to the skin, or are delivered by directed means, to a site in need thereof.

9 Claims, No Drawings

USE OF NATURAL PLANT EXTRACTS IN COSMETIC COMPOSITIONS

FIELD OF THE INVENTION

The present invention relates to the novel use of natural plant materials, or extracts derived therefrom, in cosmetic products for the face and body. More particularly, the present invention relates to the use of topical compositions having natural plant materials or extracts that stimulate lipid production ("lipogenesis") in the skin. Such compositions are particularly suitable for the treatment and prevention of the loss of subcutaneous fat, and in particular, facial fat loss, sagging skin, wrinkles, dry skin, and the like. The invention further relates to methods of delivery for such compositions so as to allow the active constituents to more readily penetrate the target area and treat, including prevent, reduce, ameliorate, and/or eliminate, signs of dermatological aging and to improve the aesthetic appearance of the skin.

BACKGROUND OF THE INVENTION

Cosmetic products, which enhance the appearance of skin, are increasingly in demand. Consumers are interested in mitigating or delaying the signs of chronologically or hormonally aged skin, as well as seeking alternatives to the costly and sometimes risky medical techniques currently available. Among the various changes that occur with dermatological aging, is the gradual loss of fat in the skin. The loss of fat, and in particular, facial fat, can result in a variety of undesireable conditions or symptoms including, for example, sagging skin, deepening appearance of wrinkles, dry skin, lack of skin tone, firmness, or plumpness, and thinning skin. The stimulation of fat production by novel materials is a desired benefit in cosmetic products to address such problems.

Active ingredients derived from plants and plant seeds have commonly been employed in topical compositions for a myriad of medicinal, therapeutic and cosmetic purposes. Such actives can be obtained from various parts of a plant such as seeds, needles, leaves, roots, bark, cones, stems, rhizomes, callus cells, protoplasts, organs and organ systems, and meristems. Active ingredients are incorporated in such compositions in a variety of forms. Such forms include a pure or semi-pure component, a solid or liquid extract or derivative, or a solid plant matter. Plant matter may be minced, ground, crushed, or otherwise physically modified for incorporation into a composition. The functional use of these materials to stimulate lipogenensis is novel and useful for the cosmetic industry.

Safe, effective and new components of compositions to treat, prevent, reduce, inhibit, and/or improve the dermatological signs of aging, associated with the loss of subcutaneous fat, would be advantageous for the formulation of treatments and products for the skin. As described herein, novel and beneficial methods and compositions, as well as their mode of action, for the treatment of loss of facial fat and sagging skin and the like, as well as for personal care products for the skin, are provided by the present invention.

SUMMARY OF THE INVENTION

The present invention provides compositions and methods comprising plant materials, or extracts derived therefrom, newly found to be effective to treat, including prevent, reduce, ameliorate, and/or eliminate, signs and results of dermatological aging of skin, especially aging associated with the loss of subcutaneous fat, and to improve the aesthetic appearance of skin.

It is an aspect of the present invention to provide topical compositions having an extract from at least one plant, or blends of plants, or extracts, preferably a natural plant extract. In particular, the present invention is directed to extracts derived from at least one of the following plants: *Rhinacanthus nasutus, Humulus scandens, Sesbania grandiflora, Amorphophallus campanulatu, Pouzolzia pentandra*, and *Piper betel*. These plant materials have been newly found to provide treatment for loss of subcutaneous fat, and other signs of dermatological aging by stimulating lipid production in the skin.

It is another aspect of the present invention to provide topical compositions having a plant-derived active ingredient, or blends of plant-derived ingredients, that stimulate lipid production in a cosmetically or dermatologically acceptable vehicle.

It is still another aspect of the present invention to provide a topical composition that delivers a plant derived active ingredient, or blends of plant-derived active ingredients, together with an effective level of a cosmetic, dermatologic, or pharmaceutic active ingredient.

Topical compositions for treating the symptoms related to the loss of subcutaneous fat are also provided. These compositions have a cosmetically, dermatologically, or pharmaceutically effective amount of at least one plant material or, extract derived therefrom, sufficient to stimulate lipid production, adiponectin production, adipocyte differentiation, and/or PPAR-gamma induction, and/or any combination thereof, and a cosmetically, dermatologically, or pharmaceutically acceptable vehicle.

It is a further aspect of the present invention to provide methods for topically applying such compositions.

It is a still further aspect of the present invention to provide methods of improving the appearance of skin, including treating the effects of aging, and stimulating lipid production in the skin, by topically applying the compositions of the invention to the skin.

It is to be understood that, as used herein, the terms treating and treatment include and encompass preventing, reducing, ameliorating, improving, alleviating, and/or eliminating the dermatological effects of aging, with particular regard to loss of subcutaneous fat, and in particular, facial fat loss and sagging skin, and the like. The present compositions and methods are also suitable for use in treating, as defined above, dermatological conditions of the skin in numerous areas of the body, including, without limitation, the face, forehead, lips, neck, arms, hands, legs, knees, feet, chest, back, groin, buttocks, and the like. In a preferred embodiment, the compositions are applied to the face.

The present compositions alleviate symptoms or conditions, including, but not limited to: loss of subcutaneous fat, loss of facial fat, sagging skin, wrinkles, dry skin, lack of skin tone, firmness, or plumpness, and/or thinning skin.

In accordance with this invention the extracts comprise compositions which include, without limitation, topically applied sunscreens, anti-oxidants, anti-inflammatories, cosmetics, including makeups, anti-aging formulations, e.g, creams for fine lines and/or wrinkles, topicals, skin permeants, and the like. Also in accordance with this invention, ingredients, components, or compounds that are formulated in such compositions in a variety of product forms, e.g., transdermals, such as patches, and the like, are encompassed, particularly for topical administration.

Another aspect of the present invention provides the compositions comprising the extracts preferably for topical administration without inducing significant irritation. Further, such compositions are preferably delivered by, but not limited to, the use of targeted delivery systems, for example, liposomes, microspheres, transdermal patches, and the like, so that the active agents can more readily penetrate the skin layer of the area of application, e.g., face or neck, or the subcutaneous layer of the skin, where adipocytes (i.e. fat cells) are located. Compositions comprising plant constituents, including liposome formulations, are preferably administered topically.

Another aspect of this invention provides a method of reducing, preventing, treating, or ameliorating loss of subcutaneous fat in the skin, comprising: applying a composition comprising an extract to the skin in an amount effective to stimulate lipogenesis, thereby treating, preventing, reducing, ameliorating, or eliminating the loss of subcutaneous fat.

Further aspects, features and advantages of the present invention will be better appreciated upon a reading of the detailed description of the invention.

DESCRIPTION OF THE INVENTION

The present invention provides novel compositions and methods comprising components newly found to be effective to treat, including prevent, reduce, ameliorate, inhibit, alleviate, and/or eliminate signs and results relating to the dermatological aging of skin due to chronological and/or hormonal aging and/or photo-aging, and/or to improve the aesthetic appearance of skin.

More specifically, the natural plant materials, or extracts derived therefrom, (also referred to as components, active agents, constituents, ingredients, reagents, substances, or compounds herein) of this invention are obtained from at least one of the following plants: *Rhinacanthus nasutus, Humulus scandens, Sesbania grandiflora, Amorphophallus campanulatu, Pouzolzia pentandra*, and *Piper betel*. These plant materials have been newly found to provide treatment for loss of lipid, and in particular, subcutaneous fat, and other signs of dermatological aging by stimulating lipid production in the skin. These plant materials have been newly determined to be effective agents in compositions and methods for treatment.

The stimulation of lipid production by novel materials is a desired benefit in cosmetic products to address such problems as facial fat loss, sagging skin, dry skin, wrinkles, and the like. Fat production is stimulated by a process known as lipogenesis (or lipid synthesis). The functional use of these materials to stimulate lipogenensis is novel and useful for the cosmetic industry.

According to the present invention, yet without wishing to be bound by theory, the extracts described herein exert their effectiveness by preferably stimulating the chemical pathways involved in lipid production and adipocyte maturation. More specifically, the extracts stimulate lipid production (e.g. total triglyceride production) in normal human adipocytes, increase adiponectin production, induce adipocyte differentiation and maturation, and activate PPAR-gamma genes responsible for differentiation and energy storage in adipocytes (see Example 2). The result of stimulating these pathways is the production of lipid, especially subcutaneous fat, thereby treating the aging effects of fat loss, especially subcutaneous facial fat loss, sagging skin, and the like.

The present invention in its broadest view encompasses the use in any topical cosmetic, dermatological, or pharmaceutical composition of any convenient plant extract or ingredient that stimulates lipid production, adiponectin production, adipocyte differentiation, and/or PPAR-gamma induction to alleviate or treat any visible or subjective effects caused by loss of fat in the skin.

The present invention also provides for compositions to improve the aesthetic appearance of skin, including ameliorating or treating the effects of aging. These benefits are manifest by one or more of the following: improvement in skin tone, radiance, clarity and/or tautness; improvement in skin firmness, plumpness, suppleness, and/or softness; improvement in skin texture and/or promotion of skin retexturization; improvement in appearance of skin contours, hollow cheeks, sunken eyes, restoration of skin luster and/or brightness; replenishment of essential nutrients and/or constituents in the skin decreased by aging and/or menopause; increase in cell proliferation and/or multiplication; increase in cell metabolism decreased by aging and/or menopause; improvement in skin moisturization; enhancement of skin thickness; reducing skin sensitivity; and an increase in skin elasticity and/or resiliency. By increasing the amount of subcutaneous fat, the extracts may also treat, prevent, reduce, ameliorate, and/or eliminate aesthetically displeasing wrinkles, frown lines, fine lines, folds, furrows, or neck bands, etc. that can arise from aging.

For purposes of the invention, the natural plant extract may be in any form including, but not limited to, an aqueous extract, a solvent-based extract, a dried extract, or combinations thereof.

In a preferred embodiment, the present compositions preferably have a concentration of plant extract of from about 0.0001 wt % to about 50 wt %, and preferably about 0.001 wt % to about 20 wt %, more preferably 0.01 wt % to about wt 2%, and even more preferably to about 0.05 to 1%, based on the total weight of the composition. One of ordinary skill in the art would be able to adjust the amount of extract used based upon the specific application or effect desired.

In another embodiment, the plant extract as used herein, also includes "synthetic" extracts, i.e. various combinations of known plant components and/or constituents that are combined to substantially mimic the composition and/or activity of a plant extract of natural origin. Such synthetic extracts are included in the term "plant extract". The synthetic extracts will have two or more, three or more, or four or more active ingredients in common with a plant. Most preferably, the synthetic extracts will have substantially the same number of active ingredients as a natural extract. The correspondence of the numerical incidence of active ingredients between the synthetic extracts and the plant or a natural extract may also be described in terms of "percent commonality". Preferably, the synthetic extract has about 50 percent or more commonality to the chemical composition of a plant or natural extract. In other words, the synthetic extract has about 50 percent or more of the active ingredients found in the plant or a natural extract. More preferably, the chemical composition of the synthetic extract has about 70 percent or more commonality to the chemical composition of a plant or a natural extract. Optimally, a synthetic extract has about 90 percent or more commonality to the chemical composition of a plant or a natural extract. The plant or natural extract for comparison is derived, most preferably, from at least one of the following plants: *Rhinacanthus nasutus, Humulus scandens, Sesbania grandiflora, Amorphophallus campanulatu, Pouzolzia pentandra*, and *Piper betel* plant.

For use in the compositions of this invention, the plants or components and/or active constituents are preferably derived directly from the plants. The components may be in a pure form, a semi-pure form, or unpurified form. In a preferred embodiment, the components are in the form of an extract obtained by organic solvent extraction (Example 1).

Briefly, the organic solvent extraction method involves washing and extracting the plant material using an organic solvent. Non-limiting examples of organic solvents include methanol, ethanol, isopropanol, dichloromethane, chloroform, hexane, xylene, and petroleum ether. An extracting machine may be used for organic solvent extraction as is well known in the field.

Organic solvent extraction involves collecting the raw materials from the plant that contain the desired constituent(s), such as seeds, needles, leaves, roots, bark, cones, stems, rhizomes, callus cells, protoplasts, organs and organ systems, and meristems. These plant materials are ground to small particle sizes, and then put into an extracting machine through an inlet for the raw materials by a measurable charging machine. The plant raw material is pushed in the extracting machine by a thruster, and slowly moves the plant raw material forward. Organic solvent (e.g., ethanol) may be added into the machine through a solvent inlet at the top of a waste discharge outlet. Due to the difference in gravity and equilibrium, the solvent flows toward the raw material inlet, soaks the materials and flows out from the opposite side of the solvent inlet. Since the plant materials and the solvent move in opposite directions against each other, the plant materials are constantly immersed in a solution that contains a low-concentration of extract. As a result of equilibrium, high yield of plant constituent(s) may be achieved by continuously extracting the plant material against the low-concentration solution.

An extraction time adapted to remove the plant constituents is suitable, with between about 1-8 hours typical, more preferably is between about 2-6 hours, and most preferably is between about 3-5 hours. The temperature of extraction is between about 30° C.-90° C., preferably between about 40° C.-70° C., and more preferably between about 50° C.-60° C. The collected extract is then fine-filtered to remove debris, and may be used directly, or is concentrated, for example by distilling the solvent or by other conventional processing, and the extract can also be provided in powder form.

Similarly, aqueous-organic solvent extraction involves initially collecting raw materials from a plant containing the desired alkaloid(s), such as seeds, needles, leaves, roots, bark, cones, stems, rhizomes, callus cells, protoplasts, organs and organ systems, and meristems of the plant, which are ground into small particle sizes. The ground plant material is soaked in aqueous solution that is acidic or alkaline, depending on the solubility and stability of the desired extract under acidic or alkaline (basic) conditions. For extraction under acidic conditions, an acid such as hydrochloric acid or sulfuric acid is added to water, e.g., at a concentration of about 3% (w/v). For extraction under alkaline conditions, an alkali such as sodium hydroxide or sodium carbonate is added to water. The extraction time and temperature of extraction are typically similar to that used in the organic solvent extraction method described above.

The extract is then collected and fine-filtered to remove debris. Alkaline agents (e.g., ammonia) or acidifying agents (e.g., sulfuric acid) may be added to the extract to neutralize the solution by adjusting the pH, depending on the acidity or alkalinity of the collected extract. The aqueous extract may be used directly, concentrated or dried. The Alternatively, organic solvent may then be added to the neutralized solution to transfer the extract actives from an aqueous phase to an organic phase. Examples of such organic solvents include, but are not limited to, ethanol, isopropanol, butanol, pentanol, hexanol and xylene. The extract comprising the transferred extract actives dissolved in organic solvent may be used directly, used as a concentrate, or dried.

Different plants containing different constituents may be mixed and extracted together. This process of mixed extraction may preferably be used for extracting those plants containing constituents having similar solubility in the solvent used for extraction, such as ethanol. The mixture of extracts may be concentrated and stored in an appropriate solvent.

In accordance with this invention, the components from the plants comprise compositions which include, without limitation, topically applied formulations, anti-oxidants, anti-inflammatories, sunscreens, cosmetics, including make-ups, anti-aging formulations, e.g., creams for fine lines and/or wrinkles, topicals, skin penetration enhancers, sprays, and the like. Also in accordance with this invention, the plant components and additional ingredients comprising such compositions can be formulated in a variety of product forms. Preferably, the compositions are prepared in targeted delivery systems, e.g. creams, lotions, gels, serums, transdermal patches, and the like, particularly for topical administration. Targeted delivery and/or penetration enhancement may also be achieved by iontophoresis.

The present invention further provides the compositions comprising the plant components preferably for topical administration or for targeted delivery without inducing significant irritation. Thus, the inventive compositions are especially suitable for sensitive skin. The compositions are applied to the skin for a period of time sufficient to improve the aesthetic appearance of skin. The compositions are preferably applied topically once, twice, or more daily, preferably, once daily. The daily application is preferably for a period of one week, two weeks, four weeks, or more. The compositions can be formulated into liposomes which can comprise other additives or substances, and/or which can be modified to more specifically reach or remain at a site following administration.

The present invention encompasses compositions comprising a cosmetically or dermatologically acceptable formulation which is suitable for contact with living animal tissue, including human tissue, with virtually no adverse physiological effect to the user. Compositions embraced by this invention can be provided in any cosmetically and/or dermatologically suitable form, preferably as a lotion or cream, but also in an anhydrous or aqueous base, as well as in a sprayable liquid form. Other suitable cosmetic product forms for the compositions of this invention include, for example, an emulsion, a lip balm, a lip gloss, a lotion, a mask, an ointment, a mousse, a patch, a pomade, a solution, a spray, a wax-based stick, or a towelette. In addition, the compositions contemplated by this invention can include one or more compatible cosmetically acceptable adjuvants commonly used and known by the skilled practitioner, such as colorants, fragrances, emollients, humectants, preservatives, vitamins, chelators, thickeners, anesthetics, anti-allergenics, antifungals, antimicrobials, other anti-inflammatory agents, antioxidants, antiseptics, depigmenting agents, film formers, insect repellents, pharmaceutical agents, photostabilizing agents, sunscreens, stabilizers, surfactants, thickeners, viscosity modifiers, and the like, as well as other botanicals such as aloe, chamomile, and the like, and as further described below.

Cosmetically or dermatologically acceptable vehicles that can be used in the present topical compositions include, but are not limited to, one or more aqueous systems, glycerins, C1-4 alcohols, fatty alcohols, fatty ethers, fatty esters, polyols, glycols, vegetable oils, mineral oils, liposomes, laminar lipid materials, silicone oils, water or any combinations thereof.

In the present invention, the vehicle may be in the form of an aqueous phase, an oil phase, a gel, a wax-in-water emulsion, a silicone-in-water emulsion, a water-in-silicone, an oil-in-water emulsion, or a water-in-oil emulsion. The aqueous phase is a mixture of one or more water soluble or water dispersible ingredient, which can be liquid, semi-solid or solid at room temperature (25° C.). The vehicle comprises or can be in the form of a suspension, dispersion or solution in water or an aqueous-alcoholic vehicle, which may contain a thickener or gellant. A person skilled in the art can select the appropriate product form, the ingredients contained therein, as well as the method for preparing it, on the basis of the knowledge that the skilled artisan possesses.

The composition may include an aqueous phase which may contain water or a mixture of water and at least one hydrophilic organic solvent such as an alcohol, especially a linear or branched lower monoalcohol containing from 2 to 5 carbon atoms, e.g., ethanol or propanol; a polyol, e.g., propylene glycol, sorbitol, glycerol, diglycerol, panthenol, or polyethylene glycol, and mixtures thereof. This aqueous phase may represent from 0.5 to 99.99 wt. % by weight of the composition.

When the composition of the invention is in the form of an emulsion, it can also optionally comprise a surfactant, preferably in an amount of from 0.1 to 30% and in particular from 1 to 20 wt. % by weight of the composition.

The composition can also comprise a thickening polymer such as an amphiphilic polyurethane, a polyacrylic homopolymer or copolymer, a polyester, and/or a hydrocarbon-based resin. The polymers can be dissolved or dispersed in the cosmetically acceptable vehicle and optionally combined with a plasticizer.

The composition of the invention may also comprise an oil phase containing oil soluble or oil dispersible ingredients that are liquid at room temperature (25° C.) and/or oily or waxy substances that are solid at room temperature, such as waxes, semisolids, gums, and mixtures thereof. This oily phase may also contain organic solvents.

Suitable oily materials that are liquid at room temperature, often referred to as oils, include hydrocarbon-based oils of animal origin such as perhydrosqualene; hydrocarbon-based plant oils such as liquid triglycerides of fatty acids of 4 to 10 carbon atoms, for instance, heptanoic or octanoic acid triglycerides, or oils such as sunflower oil, corn oil, soybean oil, grapeseed oil, castor oil, avocado oil, caprylic/capric acid triglycerides, jojoba oil; linear or branched hydrocarbons of mineral or synthetic origin such as liquid paraffins and derivatives thereof, petroleum jelly; synthetic esters and ethers, in particular esters of fatty alcohols, namely; for example, isopropyl myristate, 2-ethylhexyl palmitate, 2-octyldodecyl stearate, isostearyl isostearate; hydroxylated esters such as isostearyl lactate, octyl hydroxystearate, octyidodecyl hydroxystearate, heptanoates, octanoates and decanoates of fatty alcohols; polyol esters such as propylene glycol dioctanoate, neopentyl glycol diheptanoate, diethylene glycol diisononanoate, and pentaerythritol esters; fatty alcohols containing from 12 to 26 carbon atoms such as octyldodecanol, 2-butyloctanol, 2-hexyldecanol, 2-undecylpentadecanol, oleyl alcohol; partially hydrocarbon-based fluoro oils and/or fluorosilicone oils; silicone oils such as volatile or non-volatile, linear or cyclic polymethylsiloxanes (PDMS) that are liquid or semisolid at room temperature such as cyclomethicones and dimethicones, optionally comprising a phenyl group, for instance phenyl trimethicones, siloxanes, and mixtures thereof. These oils are usually present in an amount of 0 to about 90 wt. %, preferably from about 1 to 80 wt. % by weight of the oil phase.

The oil phase of the composition of the invention may also comprise one or more cosmetically acceptable organic solvents. These solvents are present in an amount of 0 to about 60 wt. %, preferably about 1 to 30 wt. % by weight of the composition and can be selected from the group consisting of lipophilic organic solvents, amphiphilic organic solvents and mixtures thereof. Suitable solvents which can be used in the composition of the invention include acetic acid esters such as methyl, ethyl, butyl, amyl or 2-methoxyethyl acetate; isopropyl acetate; hydrocarbons such as toluene, xylene, p-xylene, hexane or heptane; ethers containing at least 3 carbon atoms, and mixtures thereof.

The composition of the invention may further comprise any ingredient conventionally used in the cosmetic field. These ingredients include preserving agents, aqueous phase thickeners (polysaccharide biopolymers, synthetic polymers) and fatty-phase thickeners, fragrances, hydrophilic and lipophilic active agents, and mixtures thereof. The amounts of these various ingredients are those conventionally used in the cosmetic field to achieve their intended purpose, and range typically from about 0.01 to 20 wt. % by weight of the composition. The nature of these ingredients and their amounts must be compatible with the production of the compositions of the invention.

The composition of the invention may also comprise an additional particulate phase, typically present in an amount of 0 to about 30 wt. % by weight of the composition, preferably from about 0.05 to 20 wt. %, and which can comprise pigments and/or pearlescent agents and/or fillers used in cosmetic compositions. Suitable inorganic pigments include titanium oxide, zirconium oxide and cerium oxide, as well as zinc oxide, iron oxide, chromium oxide and ferric blue. Suitable organic pigments include barium, strontium, calcium, and aluminium lakes and carbon black Suitable pearlescent agents include mica coated with titanium oxide, with iron oxide, or with natural pigment. Fillers are normally present in an amount of 0 to about 20 wt. % by weight of the composition, preferably about 0.1 to 10 wt. %. Suitable fillers include talc, silica, zinc stearate, mica, kaolin, nylon (in particular orgasol) powder, polyethylene powder, Teflon, starch, boron nitride, copolymer microspheres such as Expancel (Nobel Industrie), Polytrap (Dow Coming), and silicone resin microbeads (Tospearl from Toshiba).

The oil phase of the compositions of the invention may comprise one or more waxes, gums, or mixtures thereof. The waxes include hydrocarbon-based waxes, fluoro waxes and/or silicone waxes and can be of plant, mineral, animal and/or synthetic origin. In particular, the waxes have a melting point of greater than 25° C., preferably greater than 45° C. The compositions of the present invention may contain from 0 to about 20 wt. % waxes by weight of the composition. The gums are generally high molecular weight PDMSs or cellulose gums or polysaccharides and the semisolid materials are generally hydrocarbon-based compounds such as lanolins and derivatives thereof or alternatively PDMSs. The compositions of the present invention may contain from 0 to about 20 wt. % gums by weight of the composition, typically from about 0.1%. to 10 wt. %.

The compositions of the present invention yield improvements to the aesthetic appearance of the skin by treating dermatological aging, especially chronological, actinic or hormonal aging. In particular, improvements to the aesthetic appearance of skin include at least one of the following: improvement in skin tone, radiance, clarity and/or tautness; improvement in skin firmness, plumpness, suppleness, and/or softness; improvement in skin texture and/or promotion of skin retexturization; improvement in appearance of skin contours, hollow cheeks, sunken eyes, restoration of skin luster and/or brightness; replenishment of essential nutrients and/or constituents in the skin decreased by aging and/or menopause; increase in cell proliferation and/or multiplication;

increase in cell metabolism decreased by aging and/or menopause; improvement in skin moisturization; enhancement of skin thickness; reducing skin sensitivity; and an increase in skin elasticity and/or resiliency. By increasing the amount of subcutaneous fat, the extracts of the invention may also treat, prevent, reduce, ameliorate, and/or eliminate aesthetically displeasing wrinkles, frown lines, hallow cheeks, sunken eyes, fine lines, folds, furrows, or neck bands, etc. that can arise from aging.

Also, embraced by the present invention are transdermal modes of delivery, such as patches and the like, with or without a suitable penetration enhancers. The methods and compositions embodied by the invention provide a means by which the components can be effectively administered in a transdermal system. Accordingly, a transdermal means of delivering a composition or formulation (often with a penetration enhancing composition) to the skin is that of the transdermal patch or a similar device as known and described in the art. Examples of such devices are disclosed in U.S. Pat. Nos. 5,146,846, 5,223,262, 4,820,724, 4,379,454 and 4,956,171; such descriptions are not meant to be limiting. The transdermal mode of storing and delivering the compositions onto the skin and forming the active composition is convenient and well suited for the purposes of an embodiment of the present invention. In a preferred method, the application is through a sustained release vehicle, e.g., a topically applied sustained released patch. Preferably, when a topical patch is used, the patch is applied to the desired area for extended period of time. Preferably, the extended period of time is greater than one hour, most preferably the extended period of time is overnight, i.e., when the user is sleeping.

Another particular embodiment of the present invention is directed to the delivery of the described compositions by the use of targeted delivery systems, for example, liposomes, microspheres (see, e.g., U.S. Pat. No. 5,770,222 to Unger et al.), and the like, so that the components and/or active constituents can more readily reach and affect the subcutaneous layer of the area of application, e.g., face or neck, or the other area of the skin.

In another preferred embodiment, the topical compositions of the present invention also include at least one of the following: a skin penetration enhancer, a surface smoother, a skin plumper, an optical diffuser, a sunscreen, an exfoliation promoter, and an antioxidant. Details with respect to these and other suitable cosmetic ingredients can be found in the International Cosmetic Ingredient Dictionary and Handbook, 10th Edition (2004), published by the Cosmetic, Toiletry, and Fragrance Association (CTFA), at pp. 2177-2299, which is herein incorporated by reference in its entirety.

A surface smoother provides the functional benefits of enhancing skin smoothness and reducing the appearance of fine lines and coarse wrinkles. Examples include isopropyl myristate, petrolatum, isopropyl lanolate, silicones (e.g., methicone, dimethicone), or any mixtures thereof. The surface smoother is preferably present from about 0.1 wt % to about 50 wt % of the total weight of the composition.

A skin plumper serves as a collagen enhancer to the skin. An example of a suitable, and preferred, skin plumper is palmitoyl oligopeptide. Other skin plumpers are collagen and/or glycosaminoglycan (GAG) enhancing agents. The skin plumper is preferably present from about 0.1 wt % to about 20 wt % of the total weight of the composition.

An optical diffuser is a particle that changes the surface optometrics of skin, resulting in a visual blurring and softening of, for example, lines and wrinkles. Examples of optical diffusers that can be used in the present invention include, but are not limited to, boron nitride, mica, nylon, polymethylmethacrylate (PMMA), polyurethane powder, sericite, silica, silicone powder, talc, Teflon, titanium dioxide, zinc oxide, or any mixtures thereof. The optical diffuser is preferably present from about 0.01 wt % to about 20 wt % of the total weight of the composition.

A sunscreen protects the skin from damaging ultraviolet rays. In an illustrative embodiment of the present invention, the sunscreen would provide both UVA and UVB protection, by using either a single sunscreen or a combination of sunscreens. Among the sunscreens that can be employed in the present compositions are avobenzone, cinnamic acid derivatives (such as octylmethoxy cinnamate), octyl salicylate, oxybenzone, titanium dioxide, zinc oxide, or any mixtures thereof. The sunscreen may be present from about 1 wt % to about 30 wt % of the total weight of the composition. The addition of a sunscreen may prevent/reduce the photodegradation of the composition while in the package as well as serve to protect the skin from ultraviolet radiation.

The compositions of the present invention having sunscreen bring about additional improvements to the aesthetic appearance of skin, including at least one of the following: minimizes sunburning, minimizes tanning, and reduces redness.

The present compositions may also have one or more exfoliation promoters. Suitable examples of an exfoliation promoter that can be used in the present compositions include alpha hydroxy acids (AHA); benzoyl peroxide; beta hydroxy acids; keto acids, such as pyruvic acid, 2-oxopropanoic acid, 2-oxobutanoic acid, and 2-oxopentanoic acid; oxa acids as disclosed in U.S. Pat. Nos. 5,847,003 and 5,834,513 (the disclosures of which are incorporated herein by reference); salicylic acid; urea; or any mixtures thereof. The preferred exfoliation promoters are 3,6,9-trioxaundecanedioic acid, glycolic acid, lactic acid, or any mixtures thereof.

When the present invention includes an exfoliation promoter, the composition has about 0.5 wt % to 30 wt %, preferably about 1 wt % to about 15 wt %, more preferably about 4 wt % to about 10 wt %, and most preferably about 4 wt %, of the exfoliation promoter based on the total weight of the composition.

An antioxidant functions, among other things, to scavenge free radicals from skin to protect the skin from environmental aggressors. Examples of antioxidants that may be used in the present compositions include compounds having phenolic hydroxy functions, such as ascorbic acid and its derivatives/esters; beta-carotene; catechins; curcumin; ferulic acid derivatives (e.g. ethyl ferulate, sodium ferulate); gallic acid derivatives (e.g. propyl gallate); lycopene; reductic acid; rosmarinic acid; tannic acid; tetrahydrocurcumin; tocopherol and its derivatives; uric acid; or any mixtures thereof. Other suitable antioxidants are those that have one or more thiol functions (—SH), in either reduced or non-reduced form, such as glutathione, lipoic acid, thioglycolic acid, and other sulfhydryl compounds. The antioxidant may be inorganic, such as bisulfites, metabisulfites, sulfites, or other inorganic salts and acids containing sulfur. Compositions of the present invention may have an antioxidant preferably from about 0.001 wt % to about 10 wt %, and more preferably from about 0.001 wt % to about 5 wt %, of the total weight of the composition.

The present composition may also have one or more of the following active agents, ingredients or adjuvants: anesthetics, anti-allergenics, antifungals, antiseptics, chelating agents, colorants, demulcents, emollients, emulsifiers, fragrances, humectants, lubricants, moisturizers, pH adjusters, pigment altering agents, preservatives, stabilizers, surfactants, thickeners, viscosity modifiers, vitamins, or any mixtures thereof.

The amounts of these various substances are those that are conventionally used in the cosmetic or pharmaceutical fields, for example, they can constitute from about 0.01% to 20% of the total weight of the composition.

Nonlimiting examples of active agents for formulating into the compositions of the present invention include those reagents having an effect on the treatment of wrinkles and/or fine lines, in addition to the natural plant actives as described, such as keratolytic agents, i.e., an active agent having desquamating, exfoliant, or scrubbing properties, or an active agent which can soften the horny layer of the skin. Other examples of anti-wrinkle or anti-fine line active agents include hydroxy acids and retinoids. These agents can be formulated, for example, in amounts of from about 0.0001% to 5% by weight relative to the total weight of the composition.

Suitable hydroxy acids include, for example, glycolic acid, lactic acid, malic acid, tartaric acid, citric acid, 2-hydroxyalkanoic acid, mandelic acid, salicylic acid and alkyl derivatives thereof, including 5-n-octanoylsalicylic acid, 5-n-dodecanoylsalicylic acid, 5-n-decanoylsalicylic acid, 5-n-octylsalicylic acid, 5-n-heptyloxysalicylic acid, 4-n-heptyloxysalicylic acid and 2-hydroxy-3-methylbenzoic acid or alkoxy derivatives thereof, such as 2-hydroxy-3-methyoxybenzoic acid.

Exemplary retinoids include, without limitation, retinoic acid (e.g., all-trans or 13-cis) and derivatives thereof, retinol (Vitamin A) and esters thereof, such as retinol palmitate, retinol acetate and retinol propionate, and salts thereof.

The plant component(s) of the present invention are preferably contained in a cosmetically or dematologically acceptable vehicle, medium, diluent or carrier.

In an embodiment embracing topical application, the compositions of this invention comprise a medium (vehicle, diluent or carrier) that is compatible with human skin. The compositions can be formulated as aqueous, alcohol, or aqueous/alcohol-based solutions, ointments, lotions, gels, water-in-oil, oil-in-water, of water-oil-water triple emulsions having the appearance of a cream or gel, microemulsions, or aerosols. In addition, the compositions can be in the form of vesicular dispersions containing ionic and/or nonionic lipids, as described above. Dosage units suitable for such compositions are formulated according to the conventional knowledge and techniques used in the art.

More particularly, the compositions for topical application can be in the form of a protective care composition for the skin, preferably for the face, the neck, the hands, the feet, or other areas of the body. Nonlimiting examples include day creams or lotions, night creams or lotions, sunscreen creams, lotions, or oils, body milks, makeup (a foundation), artificial tanning compositions, depilatories, and patches.

Emulsifiers are typically present in emulsion compositions of the invention in an amount of about 0.1% to 30%, by weight and preferably from about 0.5% to 30% by weight relative to the total weight of the composition. However, not all compositions will necessarily include emulsifiers.

The plant-derived constituents exert their effectiveness according to this invention by preferably working at the site of application, e.g., the skin of face, neck, arms, feet, hands, or chest, especially in the subcutaneous layer of the skin where adipocytes are located. According to this invention, the constituents, in general, comprise plant material or extracts derived from at least one of the following plants: *Rhinacanthus nasutus, Humulus scandens, Sesbania grandiflora, Amorphophallus campanulatu, Pouzolzia pentandra*, and *Piper betel*. Prior to the present invention, these materials were not previously known or recognized to stimulate lipid production, thereby replenishing lipid loss associated with aesthetically displeasing loss of facial fat and sagging skin, wrinkles and the like, that can arise from aging due to chronological and/or hormonal aging.

In general, for the purposes of the present invention, a substance, such as a plant constituent of the described compositions, is recognized as stimulating lipogenensis when it elicits an increased production of subcutaneous fat, and/or exhibits a stimulatory effect on lipid production (tryglyceride production), adiponectin production, adipocyte differentiation, and/or PPAR-gamma induction. Production of subcutaneous fat serves to smooth out the landscape, or microrelief, of the skin, thereby effecting the prevention, amelioration, reduction, and/or eradication of sagging skin, etc caused by loss of fat.

In one embodiment, the present invention relates to the administration of an effective amount of at least natural plant constituent or composition comprised thereof to stimulate lipogenesis in the skin.

In another embodiment, the present invention encompasses a method of treating loss of subcutaneous fat, sagging skin, and/or other dermatological effects of aging, comprising applying to skin a composition containing a natural plant extract in a cosmetically and/or dermatologically acceptable medium, and in an amount effective to treat, reduce, prevent and/or ameliorate the loss of subcutaneous fat, sagging skin, and/or other dermatological effects of aging of skin. In the method the natural plant is preferably a member of the following: *Rhinacanthus nasutus, Humulus scandens, Sesbania grandiflora, Amorphophallus campanulatu, Pouzolzia pentandra*, and *Piper betel* or a combination thereof. The application of the plant containing composition is preferably topical. In addition, the composition is preferably applied via a directed mode of delivery, for example, by topical application of an aqueous composition or transdermal patch.

Another embodiment of the present invention relates to a method of improving the aesthetic appearance of skin and comprises applying to the skin, or introducing via a directed mode of delivery, a composition including one or more constituents in an amount effective to improve the aesthetic appearance of the skin. According to this embodiment, the improvement in aesthetic appearance involves the treatment of at least one condition, such as signs of dermatological aging. Dermatological aging can include chronological aging, actinic aging, hormonal aging, or any combination thereof.

As will be appreciated by the practitioner, cosmetic treatments comprising compositions containing the constituents of the invention can be carried out, for example, by topically applying the cosmetic composition as described herein according to the routine technique for administering such compositions. Routine and commonly practiced techniques encompass the application of creams, lotions, gels, sera, ointments, antiperspirants, or deodorants to the skin; spraying as a form of application is also envisioned.

EXAMPLES

The following examples describe specific aspects of the invention to illustrate the invention and provide a description of the present methods for those of skill in the art. The examples should not be construed as limiting the invention, as the examples merely provide specific methodology useful in the understanding and practice of the invention and its various aspects.

Example 1

The plants of the present invention can be extracted from natural raw materials by using the methods such as described below.

Extraction Process

An extract obtained in the form of a powder was extracted with 80% ethanol at 72 C for 30 minutes. The extract was filter sterilized with a 45 µm filter to remove paticulate matter. The filtrate was used for in vitro assays.

Materials

| Plant name | Part of plant used | Type of Extraction |
| --- | --- | --- |
| Rhinacanthus nasutus | whole plant | ethanol |
| Humulus scandens | whole plant | ethanol |
| Sesbania grandiflora | flower | ethanol |
| Amophophallus campanulatus | rhizome or underground tuber | ethanol |
| Pouzolzia pentandra | stems and leaves | ethanol |

Example 2

Various natural plant extracts of the present invention were evaluated for stimulating triglyceride production, adiponectin production, induction of adipocyte differentiation, and PPAR-gamma induction.

Lipid Production (Total Triglyceride Production)

The purpose was to measure the effects of a compound at one or two concentrations each on the differentiation of human subcutaneous preadipocytes, derived from a female liposuction patient (Lot # SL0024; Age 39.8 and BMI 28.69). Undifferentiated pre-adipocytes were cultured in 96-well plates. One day after plating, compounds were added to growth medium without differentiation inducer. The cells were treated for 7 days, with re-feeding every 2 days with growth medium including compounds. Cells lysed with a buffer containing SDS. Triglyceride is converted to glycerol and free fatty acids and the glycerol concentration is measured by addition of the detection reagent, containing microbial lipase. The optical density was read at 500 nM. At the end the treatment, 100 µl/well of the conditioned media was removed from the assay plate for incubation with the glycerol assay reagent. The optical density of each well of the new plate was measured at 540 nm. Differentiation was determined by the amount of lipid accumulation measured by total triglyceride.

Adiponectin Production

Adipocytes express a variety of proteins that function in the homeostatic control of glucose and lipid metabolism, including a 30-kDa protein known as adipocyte complement-related protein (Acrp30) or adiponectin, an adipocytokine. Secretion of adiponectin by adipocytes is enhanced by insulin stimulation, while decreased expression correlates with insulin resistance, providing support for a link between Type II diabetes and obesity. It has been suggested that the development of non-insulin dependent (type 2) diabetes may involve dysregulation of adiponectin secretion. In support of the link between obesity and type 2 diabetes, it has been shown that decreased levels of circulating adiponectin correlates with insulin resistance and that adiponectin appears to be a potent insulin enhancer linking adipose tissue and whole-body glucose metabolism.

The purpose was to measure the effects of a compound on adiponectin secretion. Human subcutaneous adipocytes were used for treatment (Lot # SL0024; Age 39.8 and BMI 28.69). Two concentrations of the test compounds were added to the cells and the secretion of adiponectin was measured after 3 days of treatment using a human adiponectin ELISA which involves a pair of specific antibodies directed against human adiponectin—one immobilized on the wells for capturing the adiponectin on the test sample and another that attaches to the captured adiponectin for detection. Adiponectin present in the test sample is sandwiched between the immobilized and the secondary antibodies and can be detected by first adding an anti-IgG antibody attached to horseradish peroxidase (HRP) and then adding the substrate that causes an enzymatic reaction of the HRP marked by a color change. The concentration of adiponectin is directly proportional to the color intensity measured at 450 nm. The concentration of the samples tested is calculated using the absorbance values of the adiponectin standard solutions assayed at the same time.

Induction of Adipocyte Differentiation (aP2)

Induction of differentiation assay examines the ability of compounds to inhibit the differentiation of preadipocytes to adipocytes. Cultured preadipocytes will be incubated in the presence of insulin (100 nM), dexamethasone (1.0 µM), isobutyl methylxanthine (0.25 mM), PPAR Gamma agonist (10 µM) and test compound. Under these culture conditions and in the presence of the test compound, there should be a substantial increase in the number of preadipocytes differentiating into adipocytes.

aP2 is a fatty acid binding protein specifically expressed in adipocytes. Its expression is tightly controlled by the transcription factor Peroxisome Proliferator Activated Receptor gamma (PPAR Gamma) that plays a critical role in adipocyte differentiation. aP2 expression is induced within 24 hours after treatment with PPAR Gamma agonists. Cells are dosed with test compounds or controls for 72 hours to obtain significant induction of aP2 mRNA. The quantity of aP2 mRNA is measured by Quantigene™ branched DNA analysis, a tool used to measure the amount of mRNA present in cells. This quantitative assay works through signal amplification rather than target amplification, can be used where very little of the target mRNA is present, does not modify the target molecule, and does not require RNA purification.

PPAR-Gamma Induction

The peroxisome proliferator-activated receptor gamma (PPAR-gamma) structurally belongs to a superfamily of nuclear transcription factors and activation of this receptor has both physiological and pathological significance, particularly in the control of lipid metabolism and inflammatory response. Nuclear hormone receptors are ligand-dependent intracellular proteins that stimulate transcription of specific genes by binding to specific DNA sequences following activation by the appropriate ligand. PPAR-gamma activity is governed by binding of small lipophilic ligands, mainly fatty acids, derived from nutrition or metabolic pathways that are often controlled by PPAR-gamma. PPAR-gamma is purported to be the centerpiece of a feed-forward pathway that favors differentiation and energy storage by adipocytes. The objective of this study was to determine the effects of herbal preparations on the activation of genes regulated by this receptor. Co-transfaction assays were performed with a PPAR-gamma expression construct and a firefly luciferase reporter harboring a PPAR-gamma response element (PPARE). Luciferase activity was determined with a Dual-Luciferase Reporter Assay system. The firefly luminescence signal was normalized based on the background control luminescence signal and the ratio of the herbal-treated wells over that from controls. As positive controls, transfected cells were treated with citiglizone (10 μM). The results of these studies are shown below in Table 1.

TABLE 1

| Sample Name | Lipogenesis induced | PPAR-γ Induced | Steroryl CoA Desaturase Induced | aP2 (Adipocyte differentiation) Induction | Total Triglygerides- Glucocorticoid |
|---|---|---|---|---|---|
| Rhinacanthus (CMU111-1) | 43.2% inc | >65% inc. | | 166.4% inc | |
| Amorphophallus (CMU115-1) | 83.6% inc | | >65% inc | 98.7% inc. | 53.41% inc. |
| Humulus Scandens | 64.6% inc. | 15-30% inc | | 323.9% inc | 177.5% inc. |
| Sesbania grandiflora (CMU 213-1) | 38.3% inc | 15-30% inc | 30-50% inc | 93.7% inc | 169.8% inc. |
| Pouzolzia pentandra (CMU 124-1) | 41.1% inc | | 50-65% inc. | | |
| Piper betel (CMU 126-2) | 139.6% inc | | | | |

The contents of all patents, patent applications, published articles, abstracts, books, reference manuals and abstracts, as cited herein are hereby incorporated by reference in their entireties to more fully describe the state of the art to which the invention pertains.

As various changes can be made in the above-described subject matter without departing from the scope and spirit of the present invention, it is intended that all subject matter contained in the above description, or defined in the appended claims, be interpreted as descriptive and illustrative of the present invention. Many modifications and variations of the present invention are possible in light of the above teachings.

What is claimed is:

1. A method for treating loss of subcutaneous fat, comprising topically administering to a subject in need thereof a composition comprising a cosmetically, dermatologically, or pharmaceutically effective amount of at least one plant extract sufficient to stimulate lipid production, adiponectin production, adipocyte differentiation, PPAR-gamma induction, and/or any combinations thereof in an amount effective to ameliorate and/or reduce loss of subcutaneous fat, wherein said at least one plant extract is obtained from *Humulus scandens, Amorphophallus campanulatu*, or *Pouzolzia pentandra*, either alone or in combination with each other; and a cosmetically, dermatologically, or pharmaceutically acceptable vehicle.

2. The method according to claim 1, wherein said composition is applied for a period of time effective to ameliorate, reduce, and/or eliminate loss of subcutaneous fat.

3. The method according to claim 1, wherein the at least one plant extract comprises *Rhinacanthus nasutus, Humulus scandens, Sesbania grandiflora, Amorphophallus campanulatu, Pouzolzia pentandra*, and *Piper betel*.

4. The method according to claim 1, wherein the composition is applied at least once daily for at least one week.

5. The method according to claim 4, wherein said at least one plant extract is present in an amount about 0.001 wt % to about 20 wt % based on the total weight of the composition.

6. The method according to claim 4, wherein said at least one plant extract is present in an amount of from about 0.005 wt % to about 5 wt % of the total weight of the composition.

7. The method according to claim 1, wherein the composition comprises a cosmetically or dermatologically acceptable vehicle, carrier or diluent.

8. The method according to claim 1, wherein the composition is applied to the face and the plant extract stimulates lipid production in the subcutaneous layer of the skin, thereby replacing fat loss due to chronological or hormonal aging.

9. The method according to claim 1, wherein the at least one plant extract further comprises *Rhinacanthus nasutus, Sesbania grandiflora*, and/ or *Piper betel*.

* * * * *